(12) United States Patent
Kawanami et al.

(10) Patent No.: US 9,018,403 B2
(45) Date of Patent: Apr. 28, 2015

(54) METHOD FOR PRODUCING TETRAHYDROPYRAN COMPOUND AND INTERMEDIATE THEREOF

(71) Applicant: Nissan Chemical Industries, Ltd., Chiyoda-ku, Tokyo (JP)

(72) Inventors: Hirotaka Kawanami, Funabashi (JP); Kana Yamaguchi, Funabashi (JP); Shota Murase, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/282,584

(22) Filed: May 20, 2014

(65) Prior Publication Data

US 2014/0256921 A1    Sep. 11, 2014

Related U.S. Application Data

(62) Division of application No. 13/264,298, filed as application No. PCT/JP2010/056670 on Apr. 14, 2010, now Pat. No. 8,765,974.

(30) Foreign Application Priority Data

Apr. 14, 2009    (JP) .................................. 2009-097773

(51) Int. Cl.
    *C07D 317/00*    (2006.01)
    *C07H 9/04*    (2006.01)
    *C07D 317/72*    (2006.01)

(52) U.S. Cl.
    CPC ................ *C07H 9/04* (2013.01); *C07D 317/72* (2013.01)

(58) Field of Classification Search
CPC ... C07D 493/04; C07D 317/20; C07D 317/72
USPC ........................................................ 549/448
See application file for complete search history.

(56) References Cited

U.S. PATENT DOCUMENTS

2007/0244187 A1    10/2007    Austad et al.

FOREIGN PATENT DOCUMENTS

WO    WO 2005/118565 A1    12/2005

OTHER PUBLICATIONS

Borch et al., "An Asymmetric Synthesis of Alcohols, Amines, and Amino Acids", J. Org. Chem., vol. 37, No. 14, 1972, pp. 2347-2349.

(Continued)

*Primary Examiner* — Nizal Chandrakumar
(74) *Attorney, Agent, or Firm* — Birch, Stewart, Kolasch & Birch, LLP

(57) ABSTRACT

Disclosed is a method for producing a tetrahydropyran compound represented by general formula (5) shown in the scheme. Accordingly, a tetrahydropyran derivative is obtained in high yield and with high selectivity without using a highly toxic reagent, and an industrially useful method for producing a tetrahydropyran derivative and an intermediate thereof can be provided. In formulae (1) to (5), $R^1$ and $R^2$ each independently represent a hydrogen atom, a linear, branched, or cyclic alkyl group, or an aromatic group which may have a substituent, and $R^1$ and $R^2$ may be combined to form an alkylene group, thereby forming a ring; and $R^3$ and $R^4$ each independently represent a hydrogen atom or a linear, branched, or cyclic alkyl group, and $R^3$ and $R^4$ may be combined to form an alkylene group, thereby forming a ring.

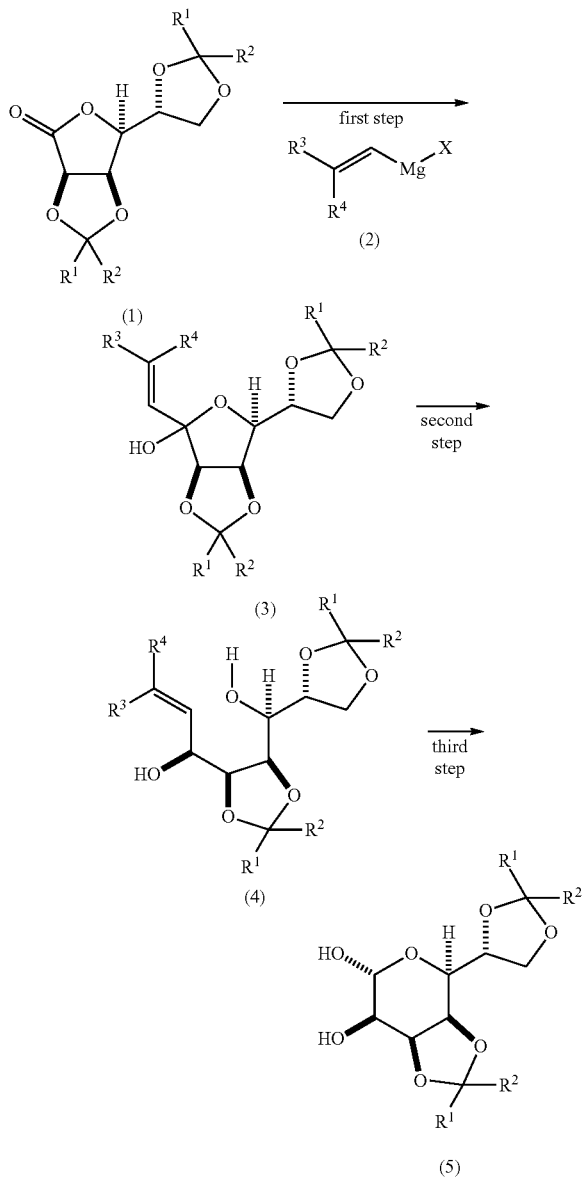

4 Claims, No Drawings

(56) References Cited

OTHER PUBLICATIONS

Calzada et al. J. Chem. Soc. Perkin Trans. I, 1995.
Choi et al., "Synthetic studies on the marine natural product halichondrins", Pure and Applied Chemistry, 2003, vol. 75, No. 1, pp. 1-17.
European Search Report dated Jul. 26, 2012 of corresponding Application No. 10 76 4474.
International Search Report, dated May 18, 2010 in PCT/JP2010/056670.
Jang et al. Chemistry Letters, (1), 67-8; 1996.
Jiang et al., "Disasteroselective Reduction of Hemiacetals Derived from 2,3-0-Isopropylidene Derivatives of Carbohydrate Lactones", Chemistry Letters, 1996, No. 1, pp. 67-68.
Kaliappan et al., "Design and synthesis of novel oxa-bridged isoxazolidines and 1,3-aminoalcohols", Tetrahedron Letters, 2005, vol. 46, No. 17, pp. 3037-3040.
Lambert et al. Journal of Organic Chemistry, 70(23), 9382-9398; 2005.
Van Hooft et al. Organic & Biomolecular Chemistry, 2(9), 1395-1403, 2004.

METHOD FOR PRODUCING TETRAHYDROPYRAN COMPOUND AND INTERMEDIATE THEREOF

CROSS REFERENCE

The present application is a 37 C.F.R. §1.53(b) divisional of, and claims priority to, U.S. application Ser. No. 13/264,298, filed Oct. 13, 2011. Application Ser. No. 13/264,298 is the national phase under 35 U.S.C. §371 of International Application No. PCT/JP2010/056670, filed on Apr. 14, 2010. Priority is also claimed to Japanese Application No. 2009-097773 filed on Apr. 14, 2009. The entire contents of each of these applications is hereby incorporated by reference.

TECHNICAL FIELD

This invention relates to a method for preparing a tetrahydropyran compound useful as a medical intermediate and also to an intermediate thereof.

BACKGROUND ART

A tetrahydropyran derivative represented by the following formula (8) is a compound that is important as a starting material such as for medicines (Patent Document 1). As an existing preparation method, there are known a method of preparing from 5-alkoxy-4-penten-1-ol (Patent Document 1) and a method of synthesizing from 5-hexen-1-ol (Non-patent Document 1).

[Chemical Formula 1]

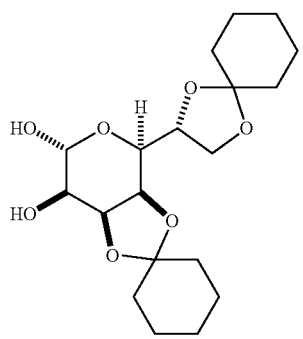

(8)

However, the preparation method of Patent Document 1 has not been accepted as a practical method because of the use of highly toxic osmium.

On the other hand, when an attempt has been made wherein the above compound is synthesized while applying the method set out in the Non-patent Document 1 as it is, it has been found that the reaction yield and steric selectivity are so low that this method is not suited for quantity synthesis.

PRIOR ART DOCUMENTS

Patent Document

Patent Document 1: WO 2005/118565 pamphlet

Non-Patent Document

Non-patent Document 1: Pure Appl. Chem., (2003), 75(1), 1-17

SUMMARY OF THE INVENTION

Problems to be Solved by the Invention

The invention has been made under such circumstances as set out above and has for its object the provision of a method for preparing an industrially useful tetrahydropyran derivative wherein the tetrahydropyran derivative can be obtained at high yield and high selectivity without use of highly toxic reagents and also of an intermediate thereof.

Means for Solving the Problems

In order to achieve the above object, the present inventors made intensive studies on a method of preparing a tetrahydropyran derivative, which is efficient and is able to attain quantity synthesis and, as a result, found an industrially suited preparation method wherein an intended product can be obtained at high yield and high steric selectivity without use of osmium of high toxicity, thereby arriving at completion of the invention.

More particularly, the invention provides

1. A method for preparing a compound represented by the following general formula (3), characterized by including reacting a compound represented by the general formula (1)

[Chemical Formula 2]

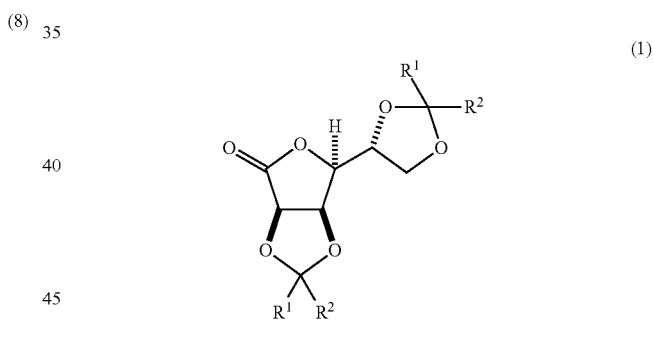

(1)

(wherein $R^1$ and $R^2$ independently represent a hydrogen atom, a linear, branched or cyclic alkyl group, or an aromatic group that may has a substituent group, provided that $R^1$ and $R^2$ may be joined to form an alkylene group thereby forming a ring), and a compound represented by the general formula (2)

[Chemical Formula 3]

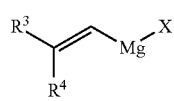

(2)

(wherein X represents a halogen atom, and $R^3$ and $R^4$ independently represent a hydrogen atom or a linear, branched or cyclic alkyl group, provided that $R^3$ and $R^4$ may be joined to form an alkylene group thereby forming a ring),

[Chemical Formula 4]

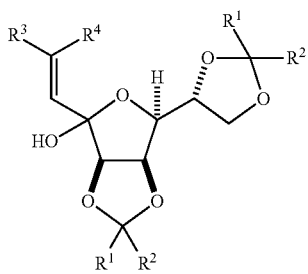
(3)

(wherein R¹, R², R³ and R⁴, respectively, have the same meanings as defined above).

2. A method for preparing a compound represented by the following general formula (4), characterized by including reducing, with a reducing agent, a compound represented by the general formula (3)

[Chemical Formula 5]

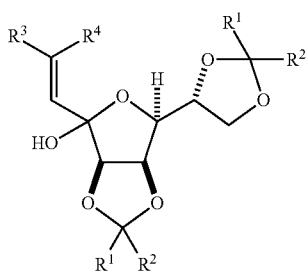
(3)

(wherein R¹ and R² independently represent a hydrogen atom, a linear, branched or cyclic alkyl group, or an aromatic group that may has a substituent group, provided that R¹ and R² may be joined to form an alkylene group thereby forming a ring, and R³ and R⁴ independently represent a hydrogen atom or a linear, branched or cyclic alkyl group provided that R³ and R⁴ may be joined to form an alkylene group thereby forming a ring),

[Chemical Formula 6]

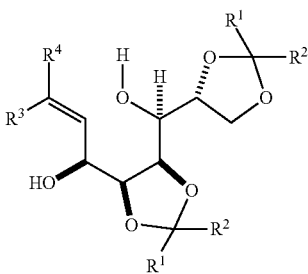
(4)

(wherein R¹, R², R³ and R⁴, respectively, have the same meanings as defined above).

3. The preparation method of 2, wherein the reducing agent is an amine borane.

4. A method for preparing a compound represented by the following general formula (5), characterized by including oxidizing a compound represented by the general formula (4) with ozone

[Chemical Formula 7]

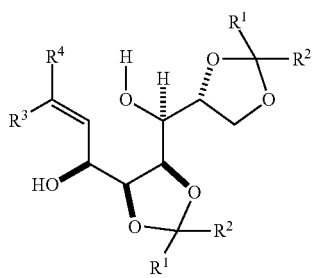
(4)

(wherein R¹ and R² independently represent a hydrogen atom, a linear, branched or cyclic alkyl group, or an aromatic group that may has a substituent group, provided that R¹ and R² may be joined to form an alkylene group thereby forming a ring, and R³ and R⁴ independently represent a hydrogen atom or a linear, branched or cyclic alkyl group, provided that R³ and R⁴ may be joined to form an alkylene group thereby forming a ring),

[Chemical Formula 8]

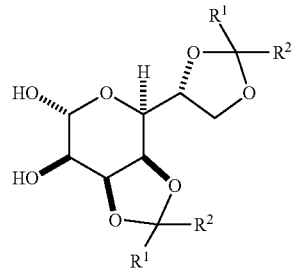
(5)

(wherein R¹ and R², respectively, have the same meanings as defined above).

5. A method for preparing a compound represented by the general formula (5), characterized by including the first step of reacting a compound represented by the general formula (1)

[Chemical Formula 9]

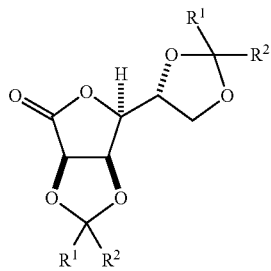
(1)

(wherein R¹ and R² independently represent a hydrogen atom, a linear, branched or cyclic alkyl group, or an aromatic group that may has a substituent group, provided that R¹ and R² may be joined to form an alkylene group thereby forming a ring), and a compound represented by the general formula (2)

[Chemical Formula 10]

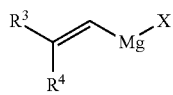
(2)

(wherein X represents a halogen atom, and R³ and R⁴ independently represent a hydrogen atom or a linear, branched or cyclic alkyl group, provided that R³ and R⁴ may be joined to form an alkylene group thereby forming a ring), thereby preparing a compound represented by the general formula (3)

[Chemical Formula 11]

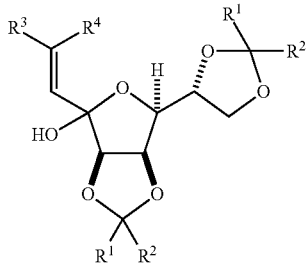
(3)

(wherein R¹, R², R³ and R⁴, respectively, have the same meanings as defined above);

the second step of reducing the compound represented by the general formula (3) thereby preparing a compound represented by the general formula (4)

[Chemical Formula 12]

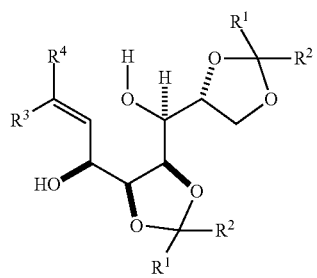
(4)

(wherein R¹, R², R³ and R⁴, respectively, have the same meanings as defined above); and the third step of oxidizing the compound represented by the general formula (4) with ozone thereby obtaining a compound represented by the general formula (5)

[Chemical Formula 13]

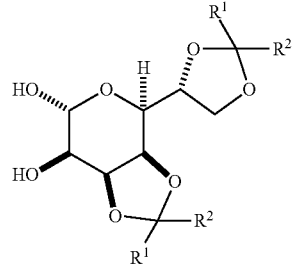
(5)

(wherein R¹ and R², respectively, have the same meanings as defined above).

6. The preparation method as recited in any of 1 to 5, wherein R¹ and R² are joined to form an alkylene group having 4 to 6 carbon atoms.

7. The preparation method as recited in any of 1 to 5, wherein R¹ and R² are joined to form an alkylene group having 5 carbon atoms and R³ and R⁴ are a hydrogen atom, respectively.

8. A compound represented by the structural formula (3)

[Chemical Formula 14]

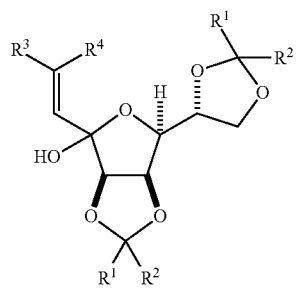
(3)

(wherein R¹ and R² independently represent a hydrogen atom, a linear, branched or cyclic alkyl group, or an aromatic group that may has a substituent group, provided that R¹ and R² may be joined to form an alkylene group thereby forming a ring, and R³ and R⁴ independently represent a hydrogen atom or a linear, branched or cyclic alkyl group, provided that R³ and R⁴ may be joined to form an alkylene group thereby forming a ring).

9. The compound of 8 represented by the structural formula (6), wherein R¹ and R² are joined to form an alkylene group having 5 carbon atoms and R³ and R⁴ are, respectively, a hydrogen atom.

[Chemical Formula 15]

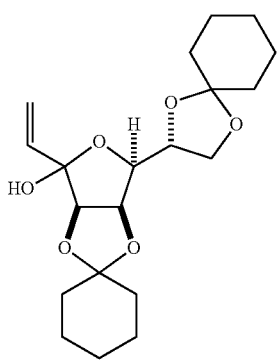

(6)

10. A compound represented by the structural formula (4)

[Chemical Formula 16]

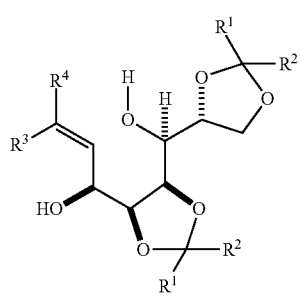

(4)

(wherein $R^1$ and $R^2$ independently represent a hydrogen atom, a linear, branched or cyclic alkyl group, or an aromatic group that may has a substituent group, provided that $R^1$ and $R^2$ may be joined to form an alkylene group thereby forming a ring, and $R^3$ and $R^4$ independently represent a hydrogen atom or a linear, branched or cyclic alkyl group, provided that $R^3$ and $R^4$ may be joined to form an alkylene group thereby forming a ring).

11. The compound of 10 represented by the structural formula (7), wherein $R^1$ and $R^2$ are joined to form an alkylene group having 5 carbon atoms and $R^3$ and $R^4$ are, respectively, a hydrogen atom.

[Chemical Formula 17]

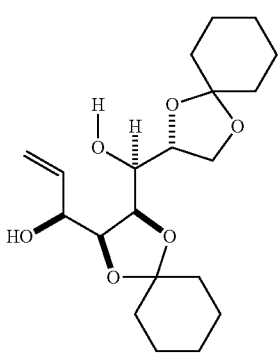

(7)

12. A method for preparing a compound represented by the following general formula (1), characterized by including reacting a D-gulonic γ-lactone compound represented by the formula (11)

[Chemical Formula 18]

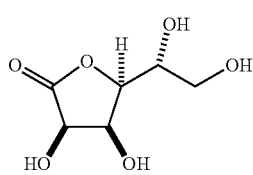

(11)

and a compound represented by the general formula (12)

[Chemical Formula 19]

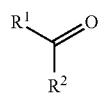

(12)

(wherein $R^1$ and $R^2$ independently represent a hydrogen atom, a linear, branched or cyclic alkyl group, or an aromatic group that may has a substituent group, provided that $R^1$ and $R^2$ may be joined to form an alkylene group thereby forming a ring), by using a p-toluenesulfonic acid/pyridine complex as a catalyst,

[Chemical Formula 20]

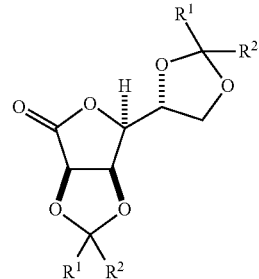

(1)

(wherein $R^1$ and $R^2$ have the same meanings as defined above).

Advantageous Effects of the Invention

According to the invention, the tetrahydropyran compound represented by the general formula (5), which is useful as a medical intermediate, can be mass-produced at high yield and high selectivity under mild conditions without use of an osmium compound, so that the preparation method of the invention is proved useful as an industrial method.

EMBODIMENT FOR CARRYING OUT THE INVENTION

The invention is now described in more detail.
It is to be noted that indicated by n is normal, by i is iso, by s is secondary, by t is tertiary, by c is cyclo, by o is ortho, by m is meta, and by p is para, respectively, whenever they appear hereinafter.

In the practice of the invention, the linear, branched or cyclic alkyl groups are not critical and are preferably ones having 1 to 10 carbon atoms. Examples include methyl, ethyl, n-propyl, i-propyl, c-propyl, n-butyl, i-butyl, s-butyl, t-butyl, c-butyl, n-pentyl, 1-methyl-n-butyl, 2-methyl-n-butyl, 3-methyl-n-butyl, 1,1-dimethyl-n-propyl, c-pentyl, 2-methyl-c-butyl, n-hexyl, 1-methyl-n-pentyl, 2-methyl-n-pentyl, 1,1-dimethyl-n-butyl, 1-ethyl-n-butyl, 1,1,2-trimethyl-n-propyl, c-hexyl, 1-methyl-c-pentyl, 1-ethyl-c-butyl, 1,2-dimethyl-c-butyl, n-heptyl, n-octyl, n-nonyl, n-decyl and the like groups.

The alkylene group formed by joining $R^1$ and $R^2$ or $R^3$ and $R^4$ is not critical and such alkylene groups having 1 to 10 carbon atoms are preferred including ethylene, trimethylene, propylene, tetramethylene, pentamethylene, hexamethylene, heptamethylene, octamethylene, nonamethylene, decamethylene and the like.

The aromatic groups that may have a substituent group include, for example, phenyl, o-methylphenyl, m-methylphenyl, p-methylphenyl, o-methoxyphenyl, m-methoxyphenyl, p-methoxyphenyl, o-trifluoromethylphenyl, m-trifluoromethylphenyl, p-trifluoromethylphenyl, xylyl, biphenyl, naphthyl and the like groups.

The halogen atoms include fluorine, chlorine, bromine and iodine atoms.

Among those substituent groups indicated above, it is preferred as $R^1$ and $R^2$ to form an alkylene group having 4 to 6 carbon atoms by joining them and more preferably to form an alkylene group having 5 carbon atoms. More particularly, tetramethylene, pentamethylene and hexamethylene groups are preferred, of which the pentamethylene group is more preferred.

$R^3$ and $R^4$ are each preferably a hydrogen atom.

X is preferably a chlorine atom or a bromine atom.

The compound represented by the general formula (X) is illustrated as abbreviated as compound (X).

The preparation method of compound (5) of the invention is shown in the following scheme. It will be noted that compound (1) serving as a starting material in the preparation method of the invention can be prepared according to the method set out in Patent Document 1.

(wherein $R^1$ to $R^4$ and X, respectively, have the same meanings as defined hereinbefore).

[1] First Step

The first step is one wherein compound (1) and compound (2) are reacted to prepare compound (3).

Although a commercially sold one may be used as compound (2), it is possible to use one that is appropriately prepared from a corresponding halide and magnesium. The halogen atom is preferably a chlorine atom or a bromine atom.

The reaction solvent is not critical provided that it is stable under reaction conditions and is so inert as not to impede the reaction.

Usable solvents include, for example, ethers (such as diethyl ether, diisopropyl ether, t-butyl methyl ether, tetrahydrofuran, dioxane and the like), aliphatic hydrocarbons (such as pentane, hexane, c-hexane, heptane, octane, decane, decaline, petroleum ether and the like), and aromatic hydrocarbons (such as benzene, toluene, xylene, mesitylene and the like) although not limited thereto. These reaction solvents may be appropriately chosen according to the ease in occurrence of reaction and may be used singly or in admixture of two or more.

In the practice of the invention, ethers are preferred and tetrahydrofuran is more preferred.

The amount of compound (2) can be within a range of about 1.0 to 1.5 molar equivalents, more preferably 1.05 to 1.20 molar equivalents, relative to unit molar equivalent of compound (1). Although the compound (2) is usually used as a commercially available tetrahydrofuran solution, other solvent, which is stable under reaction conditions and is so inert as not to impede the reaction, may be added thereto. The addition of other solvent permits easy use in the reaction system without causing a reagent to be precipitated.

Such solvents include ethers (such as diethyl ether, diisopropyl ether, t-butyl methyl ether, dioxane and the like), aromatic hydrocarbons (such as benzene, toluene, xylene, mesitylene, tetralin and the like) and alkoxyalkanes (such as dimethoxyethane, diethoxyethane and the like), of which alkoxyalkanes are preferred and dimethoxyethane is more preferred.

The amount may be within a volume of 5 to 50% of the tetrahydrofuran solution used although not limited thereto.

The reaction temperature is preferably at about −70 to 0° C., more preferably at −50 to −30° C.

The compound (1) used as a starting material in this step may be either a purified one or an unpurified one. More particularly, the reaction may be carried out by using a purified product of the compound (1) obtained according to the method set out in Patent Document 1, or by adding a solvent and a reagent used in the first step to the reaction solution of the compound (1) obtained by the method set out in Patent Document 1.

It will be noted that for the synthesis of the compound (1) accorded to the method of Patent Document 1, there may be used, aside from p-toluenesulfonic acid-hydrate, p-nitrobenzenesulfonic acid, methanesulfonic acid, p-toluenesulfonic acid/pyridine complex, benzenesulfonic acid, sulfuric acid or the like as a catalyst.

Especially, when using a p-toluenesulfonic acid/pyridine complex, an amount of the self-condensed dimer product of cyclohexanone contained in the compound (1) can be reduced from about existing 4% to 1% or below, so that where the reactions are carried out continuously, the amounts of reagents in the second and third steps can be saved.

[2] Second Step

The second step is one wherein compound (2) is reduced with a reducing agent to prepare compound (4) (alcohol derivative).

The reducing method includes a procedure making use of a variety of reducing agents such as sodium borohydride and its analogs, lithium aluminium hydride and its analogs, triacetoxy borohydride hydride and its analogs, diborane and its analogs, alkylsilanes and analogs thereof, amine boranes and analogs thereof, and the like, or a procedure making use of a catalytic hydrogenation catalyst in an atmosphere of hydrogen.

Of these, it is preferred from the standpoints of steric selectivity and reaction yield to use an amine borane represented by $R_3N/BH_3$.

As such an amine borane represented by $R_3N/BH_3$, there may be used either commercially available ones, or those prepared by known methods. For such a preparation method, reference can be made, for example, to R. F. Borch, S. R. Levitan; J. Org. Chem., 1972, 2347. It will be noted that an amine borane may be generated in a system and used for the reaction as it is.

As $R_3N$, primary, secondary and tertiary amines may be used and both optical active materials and racemic materials may be used.

As a primary amine, mention is made of methylamine, ethylamine, n-propylamine, i-propylamine, n-butylamine, i-butylamine, t-butylamine, n-pentylamine, n-hexylamine, c-hexylamine, 2-methyl-c-hexylamine, aniline, benzylamine (phenylmethylamine), 1-phenylethylamine, 2-phenylmethylamine, 1-phenylpropylamine, 1-phenylbutylamine, diphenylethylenediamine, diphenylmethylamine, triphenylmethylamine and the like.

As a secondary amine, mention is made of dimethylamine, diethylamine, di-n-propylamine, di-1-propylamine, di-n-butylamine, di-1-butylamine, di-n-pentylamine, di-n-hexylamine, di-c-hexylamine, diphenylamine, diphenylmethylamine, di-1-phenylethylamine, di-2-phenylmethylamine, morpholine, piperidine and the like.

As a tertiary amine, mention is made of trimethylamine, triethylamine, tri-n-propylamine, tri-1-propylamine, tri-n-butylamine, tri-1-butylamine, tri-n-pentylamine, tri-n-hexylamine, tri-c-hexylamine, triphenylamine, di-1-propylethylamine and the like.

There may be used a pyrrole borane, a pyridine borane, a quinoline borane and a triazine borane complex obtained by use of pyrroles such as pyrrole, pyridines such as pyridine, quinolines such as quinoline, and triazines such as triazine as $R_3N$.

In particular, it is preferred from the standpoints of steric selectivity and reaction yield to use amine boranes obtained by use of primary amines having a relatively bulky substituent group. More particularly, it is more preferred to use $C_{1-10}$ alkylamine borane complexes having a cyclic structure or branched structure, such as t-butylamine-borane complex, 2-methyl-c-hexylamine-borane complex and the like, and α-phenyl $C_{1-4}$ alkylamine borane complexes such as 1-phenylethaneamine-borane complex and the like. It will be noted that the phenyl group of the α-phenyl $C_{1-4}$ alkylamine borane complexes may be substituted with a substituent group such as an alkyl group, an alkoxy group, an alkylthio group, a halogen atom or the like.

The amount of the reducing agent is preferably at 0.5 to 1.4 molar equivalents, more preferably at 0.5 to 1.2 molar equivalents and much more preferably at 0.7 to 1.2 molar equivalents, per unit molar equivalent of compound (3).

The reaction solvent is not critical in type so far as it is stable under reaction conditions, is inert and does not impede the reaction.

Usable solvents include alcohols (such as methanol, ethanol, propanol, butanol, octanol and the like), cellosolves (such as methoxyethanol, ethoxyethanol and the like), aprotic polar organic solvents (such as dimethylformamide, dimethylsulfoxide, dimethylacetamide, tetramethyl urea, sulfolane, N-methylpyrrolidone, N,N-dimethylimidazolidinone and the like), ethers (such as diethyl ether, diisopropyl ether, t-butyl methyl ether, tetrahydrofuran, dioxane and the like), aliphatic hydrocarbons (such as pentane, hexane, c-hexane, heptane, octane, decane, decaline, petroleum ether and the like), aromatic hydrocarbons (such as benzene, chlorobenzene, o-dichlorobenzene, nitrobenzene, toluene, xylene, mesitylene, tetralin and the like), halogenated hydrocarbons (such as chloroform, dichloromethane, dichloroethane, carbon tetrachloride and the like), alkoxyalkanes (such as dimethylethane, diethoxyethane and the like), and nitriles (such as acetonitrile, propionitrile, butyronitrile and the like) although not limited thereto. These solvents may be appropriately chosen according to the ease in occurrence of reaction and may be used singly or in admixture of two or more. In the invention, methylene chloride is preferred among them.

The reaction temperature is preferably at about 0 to 30° C., more preferably at 0 to 10° C.

The compound (3) used in this reaction may be either a purified one or one obtained in the first step without isolation. Moreover, the compound (3), which has been obtained by using, as a starting material in the first step without purification, the compound (1) synthesized according to the method of Patent Document 1, may be used without purification.

[3] Third Step

The third step is one wherein after reaction with ozone, compound (4) is further reacted with a reducing agent to prepare compound (5) (dihydropyran derivative).

The feeding method of ozone used for the reaction is not critical and mention is made, for example, of a method wherein an ozone gas generated in an ozone generator is merely bubbled in the reaction solution.

The reaction solvent is not critical in type so far as it is stable under the reaction conditions and is so inert as not to impede the reaction.

Usable solvents include alcohols (such as methanol, ethanol, propanol, octanol and the like), aliphatic hydrocarbons (such as pentane, hexane, c-hexane, octane, decane, decaline, petroleum ether and the like), aromatic hydrocarbons (such as benzene, chlorobenzene, o-dichlorobenzene, nitrobenzene, toluene, xylene, mesitylene, tetralin and the like), halogenated hydrocarbons (such as chloroform, dichloromethane, dichloroethane, carbon tetrachloride and the like), ketones (such as acetone, methyl ethyl ketone, methyl butyl ketone, methyl isobutyl ketone and the like), lower aliphatic acid esters (such as methyl acetate, ethyl acetate, butyl acetate, methyl propionate and the like), and nitriles (such as acetonitrile, propionitrile, butyronitrile and the like) although not limited thereto. These solvents may be appropriately chosen according to the ease in occurrence of reaction and may be used singly or in admixture of two or more. In the invention, lower alcohols are preferred and methanol is more preferred.

The reaction temperature may be set at −78° C. to about room temperature and is preferably at about −50 to −40° C.

As a reducing agent, there may be used lower alkyl sulfides (such as dimethyl sulfide and the like), phosphines (such as triphenylphosphine, tri-n-butylphosphine and the like), phosphite esters (trimethyl phosphite, triethyl phosphite and the like, sodium phosphite, zinc powder and the like, of which a lower alkyl sulfide is preferred and diethyl sulfide is more preferred.

The reduction reaction temperature may be at about −50 to 30° C., preferably at −5 to 10° C.

The compound (4) used in this reaction may be either a purified one or compound (4) obtained in the second step without purification. Moreover, the compound (4), which has been obtained by carrying out the second step making use of the compound (3) obtained from the compound (1) synthesized by the method of Patent Document 1 and used as a starting material of the first step without purification, can be used in the third step without purification.

For carrying out the reaction, if one equivalent or below of a base relative to the compound (4) is added, washing with an alkali aqueous solution in a work-up procedure of the second step can be omitted.

The bases used therefor include strong alkalis (such as sodium hydroxide, potassium hydroxide and the like), weak alkalis (such as sodium carbonate, potassium carbonate, sodium hydrogen carbonate and the like), and carboxylic salts (such as sodium acetate, sodium oxalate, sodium propionate and the like). Carboxylic salts are preferred and sodium acetate is more preferred.

The amount of the base is preferably at 0.01 to 1 equivalent, more preferably at 0.01 to 0.5 equivalents relative to the substrate (compound (4)).

EXAMPLES

The invention is particularly described by way of Examples and Comparative Examples and should not be construed as limited to the Examples. It should be noted that nuclear magnetic resonance spectrum ($^1$H-NMR) and liquid chromatographic (LC) analyses were carried out using the following apparatus and conditions.

[1] $^1$H-NMR
  Model: JNM-ECP300 (made by JEOL, 300 MHz)
  Measuring solvent: $CDCl_3$, $DMSO-d_6$

[2] LC
(1) LC Condition 1: Analysis of Ketal Protection Reaction
  LC: Agilent 1100
  Column: YMC Pack-Pro C18 RS 6×250 mm 5 μm
  Oven Temp.: 50° C.
  Eluent: $CH_3CN$, $H_2O$
  $CH_3CN$=40% (0 min.)→40% (2 min.)→60% (50 min.)→90% (70 min)→90% (80 min.)→50% (83 min.)→40% (90 min.) wherein the time program in parentheses indicates total hours from commencement of the analysis.
  Flow rate: 1.2 ml/minute
  Detector: UV 195 nm (2) LC Condition 2: Analysis of Grignard Reaction
  LC: Agilent 1100
  Column: YMC Pack-Pro C18 RS 4.6×250 mm 5 mm
  Oven Temp.: 50° C.
  Eluent: $CH_3CN$, $H_2O$
  $CH_3CN$=50% (0 min.)→50% (2 min.)→69% (30 min.)→90% (35 min)→90% (40 min.)→50% (43 min.)→50% (50 min.) wherein the time program in parentheses indicates total hours from commencement of the analysis.
  Flow rate: 1.2 ml/minute
  Detector: UV 195 nm (3) LC Condition 3: Analysis of Reduction Reaction
  LC: Shimadzu 20A
  Column: YMC Pack-Pro C18 RS 4.6×250 mm 5 μm
  Oven Temp.: 40° C.
  Eluent: $CH_3CN$, $H_2O$
  $CH_3CN$=35% (0 min.)→35% (2 min.)→70% (36 min.)→90% (0.01 min)→90% (6 min.)→35% (0.01 min.)→35% (10 min.) wherein the time program in parentheses indicates a time taken for a change (or fixing).
  Flow rate: 1.2 ml/minute
  Detector: UV 195 nm (4) LC Condition 4: Analysis of Ozone-Oxidation Reaction
  LC: Shimadzu 10A
  Column: L-column2 ODS 4.6×250 mm 3 μm
  Oven Temp.: 45° C.
  Eluent: $CH_3CN$, $H_2O$
  $CH_3CN$=35% (0 min.)→35% (35 min.)→95% (1 min.)→95% (14 min)→35% (1 min.)→35% (19 min.) wherein the time program in parentheses indicates a time taken for a change (or fixing).
  Flow rate: 1.2 ml/minute
  Detector: UV 195 nm

REFERENCE

Preparation of
(R)-(+)-(1)-phenylethaneamine-borane complex

A glass reaction container was purged with nitrogen, to which 10.5 g of (R)-(+)-(1)-phenylethaneamine was added and dissolved in 21.0 g of n-hexane. Thereafter, 6.58 g of dimethyl sulfide-borane was added to at 0° C., followed by agitation at room temperature for 2 hours. Subsequently, there was obtained, by filtration by suction and drying under reduced pressure, 10.60 g of (R)-(+)-(1)-phenylethaneamine-borane complex in the form of a white solid at a yield of 90.7%.

Example 1

Synthesis of Compound (6)

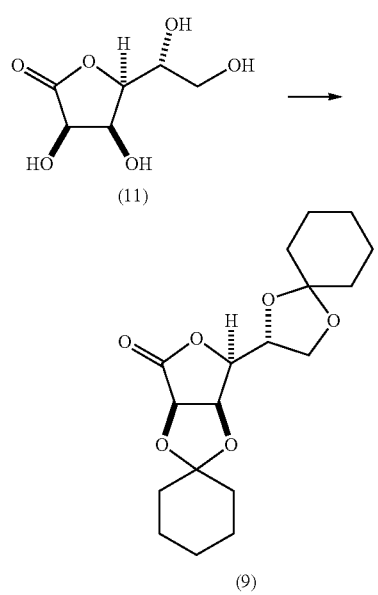

[Chemical Formula 22]

100 g of toluene was added to 10 g of D-gulonic γ-lactone and 12.12 g of cyclohexanone, to which 53 mg of p-toluenesulfonic acid monohydrate was added at room temperature.

A Dean-Stark device was attached, followed by agitation under reflux under dehydration conditions for 8 hours. Thereafter, the reaction system was cooled down to 40° C., in which 20 g of toluene and 60 g of a 1.5 wt % sodium hydrogen carbonate aqueous solution were dropped, followed by agitation for 10 minutes and phase separation. The resulting organic phase obtained by the separation was washed with 50 g of water, after which 70 g of toluene was distilled off from the organic phase under reduced pressure, followed by addition of 50 g of tetrahydrofuran to provide a toluene-tetrahydrofuran solution of compound (9). The content of compound (9) in the solution was determined by the LC analysis, revealing that an obtained amount was at 17.4 g with a yield of 92%.

Next, 15 ml of tetrahydrofuran was added to 36.75 g of the toluene-tetrahydrofuran solution containing 6.0 g of the compound (9) and cooled down to −20° C., in which a mixed solution of 21 ml of a 1.0 M vinylmagnesium bromide-tetrahydrofuran solution (made by Aldrich & Co.) and 2.1 ml of dimethoxyethane were dropped, followed by reaction for 3 hours while keeping the temperature.

The resulting reaction solution was dropped in a mixed solution of 60 ml of heptane and 60 ml of an ammonium chloride aqueous solution. After phase separation, the organic phase was washed twice with 30 g of water. The organic phase was concentrated under reduced pressure to obtain compound (6). The obtained amount of the compound (6) was 5.1 g and the yield from compound (9) was at 78%. The NMR data of the thus obtained compound (6) is shown below.

$^1$H-NMR (300 MHz, ppm, in CDCl$_3$) δ: 1.25 to 1.75 (m, 20H), 2.38 (s, 1H), 3.71 to 3.76 (dd, 1H), 4.11 to 4.15 (dd, 1H), 4.22 to 4.27 (dd, 1H), 4.35 to 4.21 (m, 1H), 4.48 to 4.50 (d, 1H), 4.73 to 4.76 (dd, 1H), 5.34 to 5.38 (dd, 1H), 5.54 to 5.60 (dd, 1H), 6.08 to 6.17 (dd, 1H)

$^{13}$C-NMR 300 MHz, ppm, in CDCl$_3$) δ: 23.7, 23.8, 23.9, 24.0, 25.0, 25.1, 34.6, 35.0, 35.8, 36.2, 65.8, 75.5, 80.3, 82.3, 86.4, 104.9, 110.4, 113.8, 117.5, 136.5

Example 2

Synthesis of Compound (7)

[Chemical Formula 23]

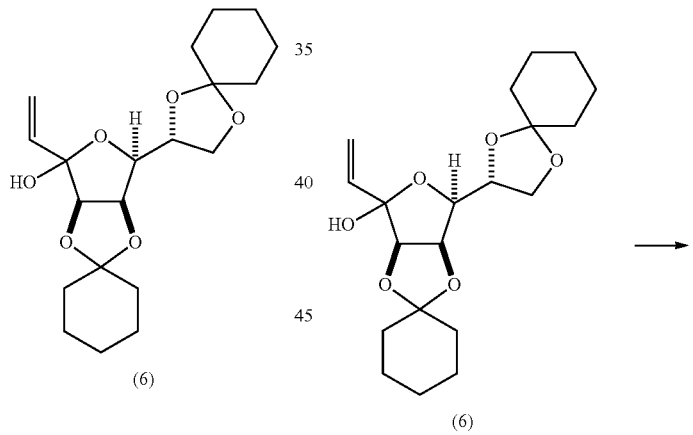

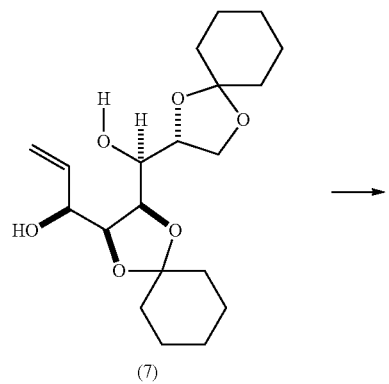

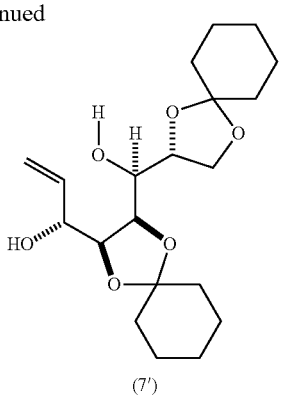

(7')

A solution of 30 g of the compound (6) obtained above and 60 g of methylene chloride was dropped in a solution of 7.12 g of tertiary butylamine-borane complex and 150 g of methylene chloride and agitated at room temperature for 20 hours.

62.6 g of a 5 wt % hydrochloric acid aqueous solution was dropped in the reaction solution and agitated at room temperature for 2 hours, followed by phase separation. 130 g of a 5 wt % sodium hydrogen carbonate aqueous solution was added to the organic phase obtained by the separation and agitated, followed by further phase separation. 90 g of water was added to the resulting organic phase and subjected again to phase separation. The thus separated organic phase was concentrated under reduced pressure to obtain compound (7). The obtained amount of the compound (7) was 23.2 g and the yield was 77%. The formation ratio between compound (7) and steric isomer (7') was at 7.9:1. The NMR data of the compound (7) are shown below.

$^1$H-NMR (300 MHz, ppm, in CDCl$_3$) δ: 1.35 to 1.75 (m, 20H), 3.02 to 3.04 (d, 1H), 3.15 to 3.17 (d, 1H), 3.81 to 3.86 (dd, 1H), 3.98 to 4.09 (m, 4H), 4.30 to 4.38 (q, 1H), 4.47 to 4.53 (m, 1H), 5.23 to 5.28 (dt, 1H), 5.37 to 5.44 (dt, 1H), 5.98 to 6.09 (ddd, 1H)

Example 3

Reduction Reaction of Compound (6)

(1) Reduction Reaction Using (R)-(+)-(1)-Phenylethaneamine-borane Complex 2.0204 g of a toluene solution of compound (6) (content of compound (6): 1.00 g) was dropped in a solution of 0.45 g of the (R)-(+)-(1)-phenylethaneamine-borane complex obtained in the reference and 5.95 g of methylene chloride and agitated at 4° C. for 20 hours. Part of the reaction solution was taken out and subjected to analysis with reverse phase HPLC, from which it was confirmed by an internal standard quantitation method that corresponding compound (7) was formed at a yield of 90.0%. The content of the compound (7) in the reaction solution was 0.90 g and the formation ratio between compound (7) and steric isomer (7') was at 19.4:1.

(2) Reduction Reaction by an In-Situ Amine Borane Generation Method 0.21 g of (R)-(+)-(1)-phenylethaneamine was added, at room temperature, to a glass reaction container that had been purged with nitrogen and dissolved in 1.00 g of toluene. Thereafter, 0.16 g of dimethyl sulfide-borane was added and agitated at room temperature for 2 hours. Subsequently, the solution was cooled down to 4° C., to which 2.96 g of methylene chloride was added, followed by dropping 1.02 g of a toluene solution of compound (6) (content of compound (6): 0.51 g) and agitating at 4° C. for 20 hours. Part of the reaction solution was taken out and subjected to analysis with reverse phase HPLC, from which it was confirmed by an internal standard quantitation method that corresponding compound (7) was formed at a yield of 86.4%. The content of the compound (7) in the reaction solution was 0.44 g and the formation ratio between compound (7) and steric isomer (7') was at 15.7:1.

The results obtained by carrying out the reduction of compound (6) in the same way as in (1) above wherein a variety of reducing agents were used are shown together in Tables 1 and 2. In the tables, indicated by the abbreviation t is tertiary, by Bu is butyl, by 9-BBN is 9-borabicyclo-[3,3,1]nonane, by Cy is cyclohexyl, by Me is methyl, by Et is ethyl, by Ph is phenyl, by 2-MeCy is 2-methylcyclohexyl group, by 1-CyEy is 1-cyclohexylethyl group, and by 1-PhEt is 1-phenylethyl group.

TABLE 1

| Reducing agent | Solvent | (7):(7') | Conversion rate (%) |
| --- | --- | --- | --- |
| tBuNH$_2$—BH$_3$ | Dichloromethane | 7.9:1 | 87 |
| Zn(BH$_4$)$_2$ | Tetrahydrofuran | 1.5:1 | 100 |
| NaBH(OAc)$_3$ | Acetonitrile | 1.4:1 | 35 |
| NaBH$_4$ | Tetrahydrofuran | 1.0:1 | 100 |
| 9-BBN | Tetrahydrofuran | 8.8:1 | 2 |
| Pyridine-BH$_3$ | Tetrahydrofuran | 8.0:1 | about 10 |
| BH$_3$—Me$_2$S | Tetrahydrofuran | 2.7:1 | 12 |

TABLE 2

| Reducing agent | Solvent | Conversion rate | (7)/(7') | Quantitative yield |
| --- | --- | --- | --- | --- |
| CyNH$_2$—BH$_3$ | Dichloromethane | 100% | 7.9 | 80% |
| 2-MeCyNH$_2$—BH$_3$ | Dichloromethane | 100% | 12.7 | 87% |
| (S)-1-CyEtNH$_2$—BH$_3$ | Dichloromethane | 100% | 12.0 | 85% |
| (R)-1-CyEtNH$_2$—BH$_3$ | Dichloromethane | 100% | 14.5 | 91% |
| (S)-(−)-1-PhEtNH$_2$—BH$_3$ | Dichloromethane | 100% | 13.5 | 86% |
| DL-1-PhEtNH$_2$—BH$_3$ | Dichloromethane | 100% | 15.6 | 88% |
| (R)-(+)-1-PhEtNH$_2$—BH$_3$ | Dichloromethane | 100% | 19.4 | 90% |

Example 4

Synthesis of Compound (8)

[Chemical Formula 24]

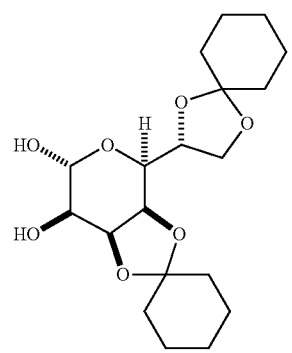

(8)

A solution of 1.59 g of the compound (7) obtained above and 15.9 g of methanol was cooled down to 0° C., into which ozone gas was blown over 30 minutes. 30 minutes after the blowing, 0.80 g of dimethyl sulfide was dropped in and agitated for 3 hours. Thereafter, the solution was raised to 55 to 58° C. to confirm the dissolution of a precipitated solid, after which the solution was cooled down to 0° C., thereby permitting a solid to be precipitated. The amount of the crystals of the resulting compound (8) was at 1.25 g with a yield of 79%.

Example 5-1

Synthesis of compound (8) from D-gulonic γ-lactone 300 g of toluene was added to 50 g of D-gulonic γ-lactone and 56.50 g of cyclohexane, to which 2.12 g of p-toluenesulfonic acid-pyridine complex was added at room temperature. A Dean-Stark device was attached, followed by agitation under reflux under dehydrating conditions for 15 hours. The reaction solution was cooled down to 50° C., to which 200 g of tetrahydrofuran was added. The content of compound (9) in the solution was determined by LC analysis, revealing that the amount was at 83.41 g and the yield was at 88%.

408 g of tetrahydrofuran was added to a toluene-tetrahydrofuran solution of the thus obtained compound (9), 222.53 g of which (content of compound (9): 18.60 g) was collected and cooled down to −30° C. 46.87 g of a vinylmagnesium chloride-tetrahydrofuran solution (made by Kanto Chemical Co., Ltd.) was dropped in the solution and the reaction conversion rate was confirmed by LC analysis, after which 8.79 g of a vinylmagnesium chloride-tetrahydrofuran solution of the same type as indicated above was dropped. After confirming the reaction conversion rate again, 1.78 g of a vinylmagnesium chloride-tetrahydrofuran solution of the same type as indicated above was dropped. After confirming the reaction conversion rate, a mixed solution of 6.44 g of acetic acid and 6.44 g of tetrahydrofuran was dropped in the reaction solution, followed by raising the temperature up to 0° C. 42.8 g of water was added to the solution, followed by phase separation to obtain an organic phase containing compound (6). According to the LC analysis, the content of the compound (6) was at 19.60 g and the yield from compound (9) was at 97%.

Subsequently, 253.7 g of the solution of the thus obtained compound (6) was collected and washed with 31.28 g of water. The resulting solution was concentrated in an evaporator to obtain 31.18 g of a solution (content of compound (6):14.33 g, LC analysis), to which 28.5 g of methylene chloride was added.

The methylene chloride solution of the compound (6) was dropped in a solution of 3.41 g of a tertiary butylamine/borane complex and 71.6 g of methylene chloride and agitated at 20° C. for 16 hours. Thereafter, 0.34 g of a tertiary butylamine-borane complex was added to the reaction solution and agitated for 1 hour. 28.2 g of a 5 wt % hydrochloric acid aqueous solution was dropped in the reaction solution and agitated at 20° C. for 2 hours, and was subjected to phase separation. 65.7 g of a 5 wt % sodium hydrogen carbonate aqueous solution was added to the resulting organic phase and agitated, followed by phase separation, and 43.0 g of water was further added to the organic phase and agitated, followed by phase separation to obtain an organic phase containing compound (7). According to the LC analysis, it was revealed that the content of compound (7) was at 8.56 g, the yield was at 59%, and the formation ratio between compound (7) and steric isomer (7') was at 6.2:1.

The resulting organic phase was concentrated, to which 63.36 g of methanol was added. This methanol solution was cooled down to 0° C., into which ozone gas was blown for 2 hours and 15 minutes (whereupon it was confirmed by LC analysis that the starting material disappeared and an ozonide intermediate was formed). After 1 hour and 30 minutes, 4.45 g of dimethyl sulfide was dropped, followed by agitation over 1.5 days (whereupon the disappearance of the ozonide was confirmed by LC analysis). Thereafter, the temperature was raised to 55 to 60° C. and after confirmation of the dissolution of a precipitated solid, the solution was cooled down to 0° C. thereby permitting a solid to be precipitated. The amount of the crystals of the resulting compound (8) was at 6.41 g and the yield was at 85%.

Example 5-2

Synthesis of compound (8) from D-gulonic γ-lactone 540 g of toluene was added to 90 g of D-gulonic γ-lactone and 101.70 g of cyclohexanone. 3.81 g of p-toluenesulfonic acid-pyridine complex was added at room temperature. A Dean-Stark device was attached, followed by agitation under reflux under dehydrating conditions for 22 hours. The solution was cooled to 40° C., to which 360 g of tetrahydrofuran was added. The determination of a content of compound (9) in the solution revealed that the amount was at 162.21 g and the yield was at 95%.

1051.11 g of the toluene/tetrahydrofuran solution of the resulting compound (9) (content of compound (9): 164.36 g) was collected, to which 824 g of tetrahydrofuran was added, followed by cooling down to −40° C. 176.33 g of a vinylmagnesium chloride-tetrahydrofuran solution (made by Kanto Chemical Co., Ltd.) was dropped in the solution and a reaction conversion rate was confirmed, after which 198.68 g of a vinylmagnesium chloride-tetrahydrofuran solution of the same type as indicated above was further dropped. After confirming the reaction conversion rate, 24.86 g of a vinylmagnesium chloride-tetrahydrofuran solution of the same type as indicated above was further dropped. After confirming the reaction conversion rate, a mixed solution of 46.08 g of acetic acid and 46.08 g of toluene was dropped in the reaction solution, followed by raising the temperature to 25° C. 379.31 g of water was added to the solution, followed by phase separation to obtain an organic phase containing compound (6). 460.77 g of a 10 wt % acetic acid aqueous solution was added to the organic phase and subjected to phase separation, and 307.18 g of a 10 wt % sodium hydroxide aqueous solution was added to the resulting organic phase, followed by further phase separation. 494.76 g of water was added to the resulting organic phase and followed by phase separation to obtain an organic phase containing compound (6). This organic phase was concentrated by means of an evaporator, to which 824.60 g of toluene was added, followed by concentration to obtain 363.30 g of a solution (content of compound (6): 156.82 g). The yield from compound (9) was at 91%.

350.00 g of a toluene solution of compound (6) (content of compound (6): 146.13 g) was dropped in a solution of 41.62 g of tertiary butylamine-borane complex and 730.63 g of methylene chloride and agitated at 4° C. for 23 hours. 581.55 g of a 3 wt % hydrochloric acid aqueous solution was dropped in the reaction solution and agitated at 30° C. for 70 minutes, after which 146.13 g of water was added to and agitated, followed by phase separation. 446.66 g of a 3 wt % sodium hydrogen carbonate aqueous solution was added to the resulting organic phase, agitated and subjected to phase separation, after which 438.38 g of water was added to the resulting organic phase and agitated, followed by phase separation to obtain an organic phase containing compound (7). This organic phase was concentrated by means of an evaporation, to which 438.38 g of methanol was added and concentrated.

Thereafter, 438.38 g of methanol was again added to the solution and concentrated, followed by further addition of 438.38 g of methanol to obtain 687.51 g of the solution. The content of compound (7) was at 130.40 g, the yield was at 82.80% and the formation ratio between compound (7) and steric isomer (7') was at 10.2:1.

674.75 g of the methanol solution of compound (7) (content of compound (7): 128.00 g) was collected, to which 1001.80 g of methanol was added, followed by cooling down to −45° C. Ozone gas was blown into the methanol solution for 3 hours and 40 minutes. After confirmation of the reaction conversion, 28.10 g of dimethyl sulfide was dropped, followed by raising the temperature to room temperature and agitating for 16 hours. Thereafter, 46.13 g of a 3 wt % sodium hydrogen carbonate aqueous solution was added to and the temperature was raised to 55 to 63° C. After confirmation of a precipitated solid being dissolved, the solution was cooled down to 0° C. to permit a solid to be precipitated. The amount of the crystals of the resulting compound (8) was at 103.12 g with a yield being at 80%.

Example 5-3

Synthesis of compound (8) from D-gulonic γ-lactone 360.42 g of toluene was added to 60.06 g of D-gulonic γ-lactone and 67.83 g of cyclohexanone, to which 2.57 g of p-toluenesulfonic acid-pyridine complex was added at room temperature. A Dean-Stark device was attached, followed by agitation under reflux under dehydrating conditions for 22 hours. The solution was cooled down to 40° C., to which 240.91 g of tetrahydrofuran was added. The determination of a content of compound (9) in the solution revealed that the obtained amount was at 110.08 g and the yield was at 96.4%.

230.39 g of the resulting toluene-tetrahydrofuran solution of compound (9) (content of compound (9): 36.24 g) was collected, to which 181.41 g of tetrahydrofuran was added, followed by cooling down to −40° C. 50.49 g of a vinylmagnesium chloride-tetrahydrofuran solution (made by Chemetall Gmbh) was dropped in the solution. After confirmation of a reaction conversion rate, 19.25 g of a vinylmagnesium chloride-tetrahydrofuran solution of the same type as indicated above was further dropped. After further confirmation of the reaction conversion rate, 2.21 g of a vinylmagnesium chloride-tetrahydrofuran solution of the same type was dropped. After confirmation of the reaction conversion rate, a mixed solution of 11.47 g of acetic acid and 11.47 g of toluene was further dropped in the reaction solution, followed by raising the temperature to 25° C. 83.11 g of water was added to the solution and subjected to phase separation to obtain an organic phase containing compound (6). 110.01 g of a 10 wt % acetic acid aqueous solution was added to the organic phase and subjected to phase separation, and 73.35 g of a 10 wt % sodium hydroxide aqueous solution was added to the resulting organic phase, followed by further phase separation. 110.08 g of water was added to the organic phase and subjected to phase separation to obtain an organic phase containing compound (6). 181.20 g of toluene was added to the organic phase and concentrated to obtain 488.70 g of a solution (content of compound (6): 37.21 g). The yield from compound (9) was at 94.8%.

170.00 g of a toluene solution of compound (6) (content of compound (6): 86.43 g) was dropped in a solution of 24.61 g of tertiary butylamine-borane complex and 432.14 g of methylene chloride and agitated at 4° C. for 23 hours. 206.38 g of a 5 wt % hydrochloric acid aqueous solution was dropped in the reaction solution and agitated at 30° C. for 2 hours, to which 210.07 g of water was added and agitated, followed by phase separation. The resulting organic phase was concentrated by an evaporator, to which 259.29 g of methanol was added and further concentrated, followed by addition of 259.29 g of methanol to obtain 432.15 g of the solution. The content of compound (7) was at 74.67 g, the yield was at 76.5% and the formation ratio between compound (7) and steric isomer (7') was at 10.2:1.

12.76 g of the methanol solution of compound (7) (content of compound (7): 2.00 g) was collected, to which 9.45 g of methanol and 0.11 g of sodium acetate were added, followed by cooling down to −45° C. Ozone gas was blown into this methanol solution for 40 minutes. After confirmation of the reaction conversion, 0.37 g of dimethyl sulfide was dropped and the temperature was subsequently raised to room temperature, followed by agitation for 16 hours. Thereafter, after confirmation of the disappearance of the intermediate, 4 g of methanol was added. Subsequently, the solution was raised to 55 to 63° C. and dissolution of a precipitated solid was confirmed, followed by cooling down to 0° C. to permit a solid to be precipitated. The amount of the crystals of the resulting compound (8) was at 1.78 g and the yield was at 78%.

Comparative Example 1

Synthesis of Compound (7) from Compound (9)

Method of Non-Patent Document 1

[Chemical Formula 25]

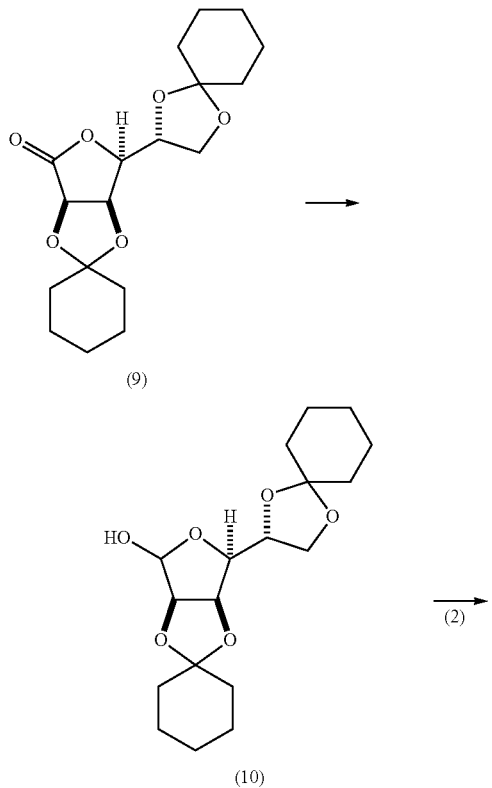

-continued

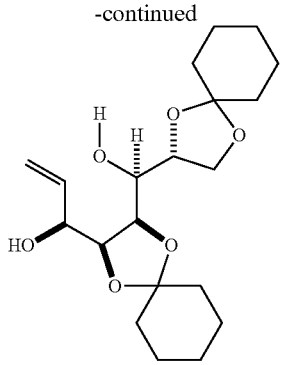

(7)

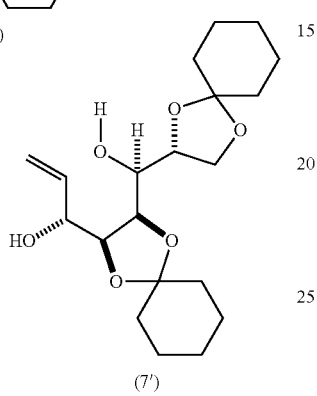

(7')

Initially, compound (10) was obtained by reducing compound (9) according to the method set forth in WO 2005/118565 pamphlet.

Next, 1.32 ml of a 1.0 M di-n-butylmagnesium-heptane solution (made by Aldrich & Co.) was dropped in a solution of 0.48 g of dicyclohexylamine and 3 ml of heptane at 65° C., followed by agitation for 30 minutes at the temperature. After confirmation of precipitation of a white solid, the solution was cooled down to room temperature, after which the heptane solvent was removed to allow the white solid to be left. 6.0 ml of tetrahydrofuran was added to the residual solid and cooled down to −60° C. A solution of 300 mg of compound (10) and 3 ml of tetrahydrofuran was dropped in the solution at −60° C. and agitated for 1 hour. Moreover, 4.4 ml of a vinylmagnesium bromide-tetrahydrofuran solution (made by Alddrich & Co.) was dropped at −60° C. and agitated for 24 hours while raising the temperature to 17° C.

The reaction solution was quenched with 15 ml of hexane and 15 ml of an ammonium chloride aqueous solution. After phase separation operations, the resulting organic phase was concentrated under reduced pressure to obtain compound (7). The amount of the compound (7) was at 148 mg, the yield was at 44% and the yield of a steric isomer (7') was at 16%.

The invention claimed is:

1. A compound represented by the structural formula (3)

(3)

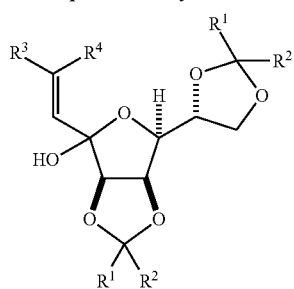

wherein $R^1$ and $R^2$ independently represent a hydrogen atom, a linear, branched or cyclic alkyl group, or an aromatic group that may has a substituent group, provided that $R^1$ and $R^2$ may be joined to form an alkylene group thereby forming a ring, and $R^3$ and $R^4$ independently represent a hydrogen atom or a linear, branched or cyclic alkyl group, provided that $R^3$ and $R^4$ may be joined to form an alkylene group thereby forming a ring.

2. The compound as defined in claim 1 represented by the structural formula (6), wherein $R^1$ and $R^2$ are joined to form an alkylene group having 5 carbon atoms and $R^3$ and $R^4$ are, respectively, a hydrogen atom (6)

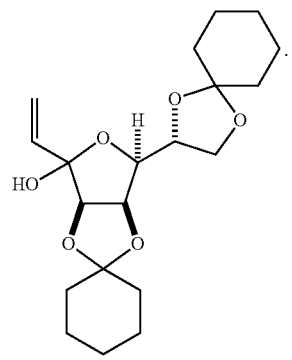

3. A compound represented by the structural formula (4)

(4)

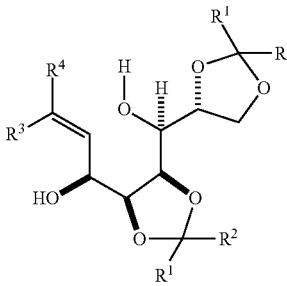

wherein $R^1$ and $R^2$ independently represent a hydrogen atom, a linear, branched or cyclic alkyl group, or an aromatic group that may has a substituent group, provided that $R^1$ and $R^2$ may be joined to form an alkylene group thereby forming a ring, and $R^3$ and $R^4$ independently represent a hydrogen atom or a linear, branched or cyclic alkyl group, provided that $R^3$ and $R^4$ may be joined to form an alkylene group thereby forming a ring.

4. The compound as defined in claim 3 represented by the structural formula (7), wherein $R^1$ and $R^2$ are joined to form an alkylene group having 5 carbon atoms and $R^3$ and $R^4$ are a hydrogen atom (7)

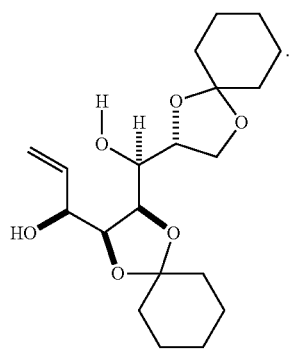

* * * * *